United States Patent [19]

Greene

[11] 4,130,909
[45] Dec. 26, 1978

[54] MIRROR CLEANING DEVICE

[76] Inventor: Shelly M. Greene, 1831 Watson Rd., Abington, Pa. 19001

[21] Appl. No.: 835,654

[22] Filed: Sep. 22, 1977

[51] Int. Cl.² .................. B05C 11/105; B08B 3/04
[52] U.S. Cl. .................. 15/104.92; 118/268
[58] Field of Search .................. 15/104.92, 423; 118/264, 268, 270; 401/198, 199; 222/187

[56] References Cited

U.S. PATENT DOCUMENTS

| 325,632 | 9/1885 | Ryder | 118/270 XR |
| 575,486 | 1/1897 | Linde | 118/268 |
| 668,053 | 2/1901 | Scattergood | 118/268 X |
| 861,309 | 7/1907 | Never | 118/268 |
| 982,939 | 1/1911 | Cummings | 118/268 X |
| 1,372,341 | 3/1921 | Dickopf | 118/268 |
| 1,705,256 | 3/1929 | Krusi | 401/198 VX |
| 2,340,204 | 1/1944 | Pike | 118/268 |
| 2,599,561 | 6/1952 | Knight | 118/268 |
| 3,095,328 | 6/1963 | Tanchuk | 118/268 |
| 3,393,416 | 7/1968 | Kilpatrick | 15/104.92 |

FOREIGN PATENT DOCUMENTS 949971  3/1949  France .................. 222/187

Primary Examiner—Daniel Blum
Attorney, Agent, or Firm—Maleson, Rosenberg & Bilker

[57] ABSTRACT

A mirror cleaning device which provides for a generally closed container having cleaning and defogging liquid maintained therein. The cleaning device includes a cup member having a cover. A liquid dispensing securement device consisting of a pair of tubular elements secured each to the other and intersecting in a substantially perpendicular manner extends through and is secured to the cover. A pair of cotton rolls are inserted within each of the tubular members into contiguous contact with each other. One of the cotton rolls is vertically directed and extends from the first tubular member, partially immersed within the cleaning liquid maintained within the cup. The second tubular member is generally horizontally directed and is partially open in contour to allow exposure of the cotton roll inserted therein. Capillary or wicking action permits the continuous flow of fluid from the liquid within the cup to the horizontally directed cotton roll where a mirror to be cleaned may be wiped across a bottom surface.

9 Claims, 4 Drawing Figures

MIRROR CLEANING DEVICE

BACKGROUND OF THE INVENTION

1. Field of the Invention

This invention pertains to cleaning devices. In particular this invention pertains to mirror cleaning devices. More in particular, this invention pertains to a mirror cleaning device which permits the cleaning and removal of condensation on a mirror in a one step operation by passage of the mirror in wiping contact with an element of the device. Still further, this invention pertains to a mirror cleaning device where the liquid dispensing element may be removed from the system in order to prevent cross contamination between various users.

2. Prior Art

Mirror cleaning systems for particular use in dental mirrors is well known in the art. In some prior systems the dentist will insert the mirror into a cleaning and defogging liquid which is merely contained in an open cup. Such open systems provide for unwanted evaporation of the cleaning liquid to the ambient environment. Thus, constant replenishing of liquid must be accomplished which is a waste of both time and materials.

In such open cup type systems, accidental spilling of the liquid is a distinct problem due to the fact that the main attention of the dentist is directed toward the oral cavity of the patient and his insert of the dental implement into the cup may through inadvertence cause a tipping over of the system. This has the disadvantage of a loss of the cleaning liquid, inconvenience in cleaning up the liquid and a loss of time in replenishing the cleaning liquid.

Such prior art open cup type cleaning systems also provide for cross contamination between individual patients since the dental mirror is being immersed into the same liquid from patient to patient. This will cause the unwanted transference of bacteria or other deleterious elements from one patient to another.

Further, in other open type prior art systems, debris may stick to the surface of the dental mirror and cannot be merely removed by immersion in the liquid. Thus, this debris must be separately wiped away and is a secondary procedure which causes a loss of time at perhaps a crucial point in a dental procedure. In other prior art open cup cleaning systems, when the dental mirror is immersed in the cleaning liquid, excess liquid may drip into the patient's oral cavity and such may be objectionable to the patient since the cleaning and defogging liquid contains sterilizing chemicals.

In other prior art dental cleaning mirror systems, a single wick or absorbent member is utilized for dispensing the cleaning liquid. In such prior art cleaning systems, the replenishing of liquid into the absorbent member and the removal of the absorbent member from the cleaning system is a complicated procedure and does not use standard materials easily obtainable in a dental office.

SUMMARY OF THE INVENTION

A mirror cleaning device which includes a cup member adapted for containing cleaning liquid therein. A cup cover member is insertable over the cup member in releasable securement thereto and has at least a first opening formed therethrough. A liquid dispensing device is partially immersed within the cleaning liquid and extends external to the cup member. A liquid dispensing securement device is mounted to the cup cover member and has a through passage aligned with the first opening in the cup cover member to provide a continuous flow passage of the cleaning liquid.

DESCRIPTION OF THE PREFERRED EMBODIMENTS

Figure 1:
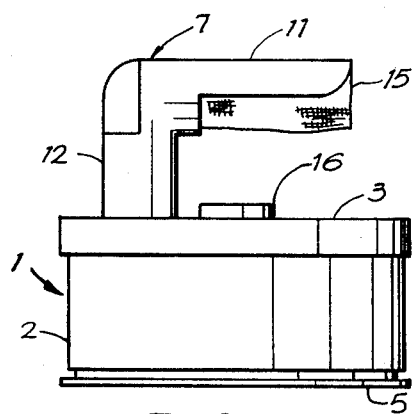
FIG. 1 is an elevation view of the mirror cleaning device.
Figure 2:
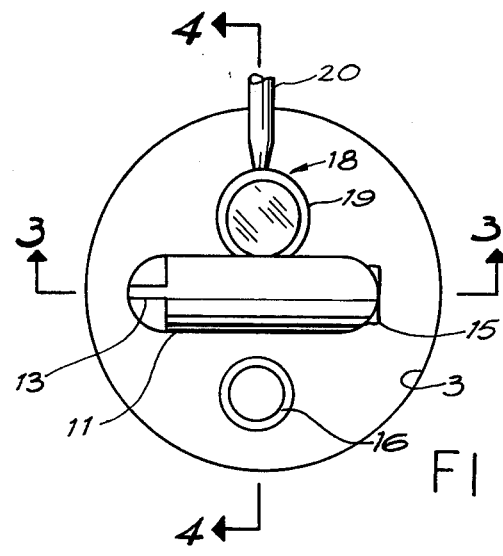
FIG. 2 is a top view of the mirror cleaning device.

Referring now to FIGS. 1-4, there is shown mirror cleaning device 1 for use in conjunction with a mirror like implement 18. Although particularly adaptable for use in dental offices, improved mirror cleaning device 1 is not to be construed as limited in use to such applications. In dental applications, dental mouth mirrors 19 have been found to be decreased in reflective efficiency due to both fogging of the surface of mirror 19 as well as debris coating as the result of a multiplicity of dental procedures. Fogging results from condensation forming on the surface of mirror 19 generally due to the differential temperatures between the mirror surface and the patient's mouth cavity environment. Due to the fact that dental mirror implements 18 may be in constant use during certain dental procedures, and that such procedures dictate that time intervals are a critical parameter with the dentist's attention drawn mainly to the patient's oral cavity, it has been found that a simply used improved mirror cleaning system 1 is of extreme value.

Figure 3:
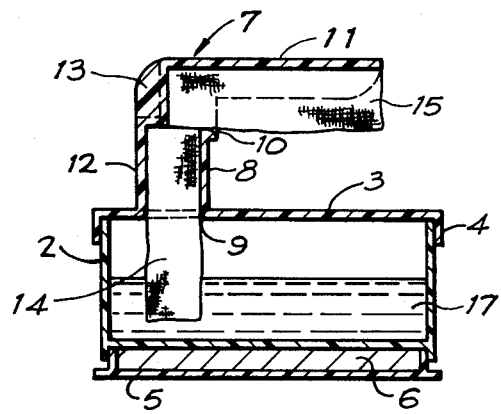
FIG. 3 is a section view of the mirror cleaning device taken along the section lines 3—3 of FIG. 2; and, FIG. 4 is a sectional view of the mirror cleaning device taken along the section lines 4—4 of FIG. 2.
Figure 4:
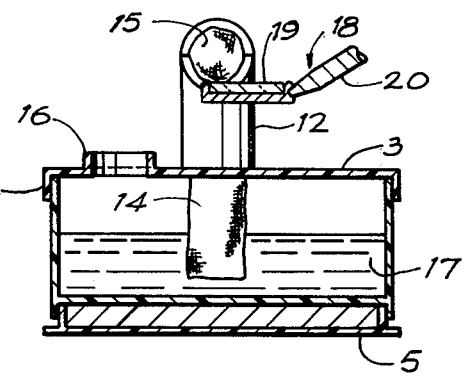

In overall concept, mirror cleaning device 1 as shown in FIGS. 1, 3 and 4 includes cup member 2 adapted for containing cleaning liquid 17 therein. Cleaning liquid 17 may be one of a plurality of cleaning and defogging liquids now commercially available on the open market. Such cleaning liquids may include benzalkonium chloride as an active ingredient. However, a number of cleaning liquid solutions 17 exist and include in general a germicide, a detergent, and a surface tension agent. Cup member 2 includes base element 5 as is seen in FIGS. 1 and 3 which in one construction may be inserted contiguous to the internal lateral side walls of cup member 2 as is shown. Base element 5 may then be secured to the lateral side walls of cup member 2 through adhesive bonding, or some like technique not important to the inventive concept as is herein described with the exception that base 5 be secured in a manner such that the possibility of leakage of cleaning liquid 17 from the internal environments of cup member 2 is negated. Base element 5 may be formed of or have secured thereto high density material 6 for lowering the positional location of the center of gravity of cleaning device 1 to prevent spillage of cleaning liquid 17. Heavy weight based material 6 may be formed of lead, steel, or some like material such that inadvertent impact loads to improved mirror cleaning device 1 would not cause sufficient dynamic inclination to allow spillage of cleaning and defogging liquid solution 17.

Cup cover member or lid 3 is insertable over cup member 2 and is in releasable securement thereto. As can be seen in FIG. 3, cover member 3 may include lid flange 4 which extends around a lateral side wall of cup member 2. The internal diameter of flange section 4 is substantially equal to but slightly greater than the external diameter of the side walls of cup 2 in order that substantially mating and contiguous contact may be made when cover member 3 is inserted over cup member 2. In this manner, lid or cover member 3 is maintained in secured position with cup 2 to provide a covering therefor, however, lid 3 may easily be removed by vertical displacement of cover member 3 from the upper wall of cup member 2.

Liquid dispensing securement device 7 is mounted to lid or cover member 3 and includes a through passage as will be described in following paragraphs to provide a continuous flow passage for cleaning and defogging liquid 17 from internal to cup member to an external environment where mirror 19 of implement 18 may be cleaned.

As is seen in FIGS. 3 and 4, liquid dispensing elements 14 and 15 are insertable within liquid dispensing securement device 7. First liquid absorbent member 14 is partially immersed in cleaning fluid 17 and extends external from cup member 2 through a first opening formed within lid or cover member 3 as is evident in FIG. 3.

First liquid absorbent member 14 is shown as being vertically directed and is insertable within a first portion of a continuous through passage formed within liquid dispensing securement device 7. As can be seen, second liquid absorbent member 15 is generally horizontally directed and is insertable within a second portion of the overall through passage formed by liquid dispensing securement device 7. Of importance, during operation, as is seen in FIG. 3, second liquid absorbent member 15 is in surface contact with first liquid absorbent member 14 in order to provide a continuous path for cleaning and defogging liquid flow from internal to cup member to an external environment.

Liquid dispensing securement device 7 is formed of first tubular member 8 which is shown as being generally vertically directed from cup cover member 3. Additionally, second tubular member 11 is generally shown to be directed in a horizontal manner and is secured to first tubular member 8. It will be noted, that first tubular and vertically directed member 8 includes closed contour outer wall 12 which defines and provides the first portion of the overall through passage of liquid dispensing securement device 7. The closed contour outer wall 12 prevents excessive evaporation as cleaning and defogging liquid 17 is drawn through wicking or a capillary action through vertically directed or first absorbent member 14.

First tubular member 8 may be formed in one piece formation with cover lid 3 or may be mounted thereto in secured relation through adhesive bonding, bolting or some like technique not important to the inventive concept as is herein described. Of importance, is that the first portion of the overall through passage as defined by first tubular member 8 is in coincident alignment with an opening formed within lid or cover member 3 in order that first absorbent member 14 may linearly pass internal to first tubular member 8 and extend at least partially into cleaning and defogging liquid 17. As is seen in FIG. 3, the internal surface of lid element 3 includes a flared portion 9 in order to provide quick and easy insert for first absorbent member 14.

Second tubular or horizontal member 11 is secured in fixed relation which may be a one piece construction to first tubular member 8. Second tubular member 11 includes an open contour outer wall when taken with respect to a circumferential surface in a plane normal to an axis line of second tubular member 11. The open contour wall extends throughout at least a section of the extended length of tubular member 11 and provides a second portion of the overall through passage for liquid dispensing securement device 7. First tubular member 8 and second tubular member 11 are seen to be secured each to the other in a substantially perpendicular alignment when taken with respect to axis lines of the extended length of each of members 8 and 11 or alternatively when taken with respect to the axis lines of the first and second portions of the overall through passage defined by the extended lengths of members 8 and 11.

As is shown, second absorbent member may be inserted into second tubular member 11 and may be grasped within a closed contour section of an outer wall of second tubular member 11. However, absorbent member 15 is exposed to the external environment throughout a section of the extended length of tubular member 11 in order to provide an extended area within which mirror 19 of implement 18 may be forced into contact therewith in order to wipe and clean the mirror surface. Thus, as is seen in FIGS. 1 and 3, throughout the open contour outer wall section of tubular member 11, the outer wall only contacts a segment of second liquid absorbent member 15 generally on an upper surface thereof.

Positionally located internal to the overall through passage and at the intersection area of first tubular member 8 and second tubular member 11, there may be placed shoulder element 13 for appropriately positioning first and second liquid absorbent members 14 and 15. Thus, first absorbent member 14 may be inserted into the first portion of the through passage of liquid dispensing securement device 7 and be forced up against a lower horizontally directed surface of shoulder 13. In similar manner, horizontally directed absorbent member 14 may be inserted into tubular member 11 and positionally located adjacent a vertically directed element section of shoulder 13. The lower horizontal surface of shoulder 13 is generally positioned slightly above the lower wall internal surface of tubular element 11 in order that surface contact may be made between elements 14 and 15 as is shown in FIG. 3.

As has been stated, first absorbent member 14 and second absorbent member 15 may be formed of a fibrous material capable of wicking or capillary action to provide dispensation of cleaning and defogging liquid 17 within cup member 2. Absorbent members 14 and 15 may be formed of cotton fibers and further may be a standard cotton roll commonly used in dental offices for a variety of purposes. Such cotton rolls are well known in the art and commercially available.

Of importance in the dispersion of cleaning and defogging liquid 17 is the consideration that liquid 17 have a continuous flow path from internal cup 2 into second absorbent cotton roll member 15. In order to accomplish this, distinct contact must be made between first cotton roll 14 and second cotton roll 15 when such are inserted within liquid dispensing securement device 7.

Opening flange member 16 is formed in a vertical direction through lid or cover member 3 as is clearly seen in FIGS. 3 and 4. Opening flange section 16 has a through opening of sufficient diameter to permit insert of a third absorbent member into liquid 17 within cup 2. Thus, a third absorbent member is inserted into cleaning and defogging liquid 17 prior to horizontal insertion within section 11 of liquid dispensing securement device 7. In this manner, the user may essentially prime the system in order to maintain a contiuous flow of liquid through the first liquid absorbing member 14 into second liquid absorbing member 15. The initial insertion of a cotton roll through flange section 16 into liquid 17 initially moistens an end of the cotton roll and allows liquid to be efficiently directed through capillary or wicking action.

In operation, a dental implement 18 being grasped by handle 20 is generally utilized internal to the oral cavity of a patient. Due to condensation and debris forming on the surface of mirror 19, such reduces the reflective efficiency thereof. The dentist may then pass mirror 19 into contiguous contact with horiztonal cotton roll 15 as is seen in FIG. 4 wherein a predetermined amount of cleaning and defogging liquid 17 is dispensed onto the surface of mirror 19. The dentist passes the mirror in compressive contact across the bottom surface of horizontal cotton roll 15 thereby causing a wiping action and removing the debris as well as the condensation from mirror 19.

After use with one patient, it is important to note that horizontal cotton roll 15 may be removed from liquid dispensing securement device 7 and a new second liquid absorbing material inserted therein. The removability and replacement of each horizontal cotton roll 15 individually with respect to each patient is important in that various bacteria and other elements would not be passed from one patient to another.

The improved mirror cleaning device 1 as is herein provided describes a substantially closed system with only horizontal cotton roll 15 being exposed to the external environment. Evaporation of cleaning and defogging liquid 17 is thus minimized since only a small surface area of horizontal roll 15 is exposed to the ambient environment. Additionally, since cup 2 and lid cover 3 provide for a generally closed container, the possibility of accidentally spilling liquid 17 is generally minimized.

Dental operations are generally increased in efficiency ratings due to the fact that cleaning debris from mirror 19 and applying liquid 17 to the mirror surface are accomplished in a one step operation where the mirror 19 is compressively wiped across horizontal roll 15. Still further the removability of horizontal roll 15 from device 7 eliminates cross contamination between individual patients.

There has been shown and described an improved mirror cleaning device for dentists in the principal form of its embodiment. It is to be understood that the foregoing is to be regarded as illustrative and descriptive only of the best known forms of the invention, but not as limitative or restrictive as to the details shown, applicant reserving the right to make such changes therein as might come within the scope of the appended claims, without thereby departing either from the spirit or the scope of the present invention.

What is claimed is:

1. A mirror cleaning device, comprising:
   (a) a cup member adapted for containing cleaning liquid therein;
   (b) a cup cover member insertable over said cup member in releasable securement thereto and having at least a first opening formed therethrough for passage of said cleaning liquid;
   (c) liquid dispensing means partially immersed within said cleaning liquid and extending external said cup member through said first opening;
   (d) liquid dispensing securement means mounted on said cup cover member and having a through passage aligned with said first opening in said cup cover member to provide a continuous flow passage of said cleaning liquid, said liquid dispensing securement means including a first vertically directed tubular member extending from said cup cover member and a second horizontally directed tubular member secured to said first tubular member, said second tubular member having an open contour outer wall throughout only a portion of said horizontally extended length for providing an enlarged mirror contact surface with said liquid dispensing means; and
   said liquid dispensing means including a first liquid absorbent member insertable within the vertically directed portion of said through passage of said liquid dispensing securement means and extending into said cleaning liquid, and a second liquid absorbent member insertable within a second horizontally directed portion of said through passage of said liquid dispensing securement means, said second liquid absorbent member contacting said first liquid absorbent member to provide a continuous path for said cleaning liquid flow.

2. The mirror cleaning device as recited in claim 1 where said first tubular member has a closed contour outer wall providing said first portion of said through passage; and, said second tubular member having said open contour outer wall throughout at least a section of an extended length of said second tubular member provides said second portion of said through passage.

3. The mirror cleaning device as recited in claim 2 where said first tubular member and said second tubular member are secured each to the other in substantially perpendicular alignment when taken with respect to axis lines of said first and second portions of said through passage.

4. The mirror cleaning device as recited in claim 2 where said first tubular member and said second tubular member are secured each to the other in one piece formation.

5. The mirror cleaning device as recited in claim 2 where said second tubular member open contour outer wall section is adapted for exposing said second liquid absorbent member to an external environment, said open contour outer wall contacting a segment of said second liquid absorbent member surface.

6. The mirror cleaning device as recited in claim 2 where said first and second liquid absorbent members are cotton rolls.

7. The mirror cleaning device as recited in claim 1 where said cup member includes a base element, said base element formed of a material of high density for lowering the positional location of the center of gravity of said cleaning system to prevent spillage of said liquid.

8. The mirror cleaning device as recited in claim 1 including a third absorbent member partially insertable into said cleaning liquid through a second opening formed through said cup cover member.

9. The mirror cleaning device as recited in claim 1 where said liquid dispensing securement means is formed in one piece construction with said cup cover member.

* * * * *